United States Patent
Tsuda et al.

(10) Patent No.: US 8,920,846 B2
(45) Date of Patent: Dec. 30, 2014

(54) MICROCAPSULE AND PRODUCTION METHOD THEREOF

(75) Inventors: Naoki Tsuda, Yokohama (JP); Mayuko Ozawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/392,534

(22) PCT Filed: Sep. 2, 2010

(86) PCT No.: PCT/JP2010/065457
§ 371 (c)(1),
(2), (4) Date: Feb. 27, 2012

(87) PCT Pub. No.: WO2011/030805
PCT Pub. Date: Mar. 17, 2011

(65) Prior Publication Data
US 2012/0156303 A1    Jun. 21, 2012

(30) Foreign Application Priority Data
Sep. 10, 2009   (JP) ................................ 2009-209063

(51) Int. Cl.
| | | |
|---|---|---|
| *A01N 25/28* | (2006.01) | |
| *A01N 43/36* | (2006.01) | |
| *A01P 15/00* | (2006.01) | |
| *A01N 43/78* | (2006.01) | |
| *A01N 43/12* | (2006.01) | |
| *A01N 43/54* | (2006.01) | |
| *A01N 43/56* | (2006.01) | |
| *A01N 51/00* | (2006.01) | |

(52) U.S. Cl.
CPC ............. *A01N 25/28* (2013.01); *A01N 43/12* (2013.01); *A01N 43/54* (2013.01); *A01N 43/56* (2013.01); *A01N 51/00* (2013.01)
USPC ........... 424/496; 514/365; 514/424; 514/521; 514/531; 424/408; 424/417; 424/490

(58) Field of Classification Search
USPC .................... 514/365, 424, 521, 531
See application file for complete search history.

(56) References Cited

U.S. PATENT DOCUMENTS

| | | | |
|---|---|---|---|
| 5,093,031 A | 3/1992 | Login et al. | |
| 5,108,991 A | 4/1992 | Rajadhyaksha | |
| 5,294,644 A | 3/1994 | Login et al. | |
| 5,328,693 A | 7/1994 | Horstmann et al. | |
| 6,255,250 B1 * | 7/2001 | Finch et al. .................. 504/138 |
| 6,294,570 B1 | 9/2001 | Krause et al. | |
| 6,426,082 B1 * | 7/2002 | Ueda et al. ..................... 424/408 |
| 2002/0028778 A1 * | 3/2002 | Aven et al. ..................... 514/24 |
| 2005/0221991 A1 * | 10/2005 | Wolf et al. ..................... 504/359 |
| 2006/0128569 A1 * | 6/2006 | Bell .............................. 504/359 |
| 2008/0207445 A1 | 8/2008 | Dexter et al. | |
| 2009/0142406 A1 | 6/2009 | Tanedani | |
| 2009/0162409 A1 | 6/2009 | Tanedani | |
| 2010/0240722 A1 | 9/2010 | Kumamoto et al. | |

FOREIGN PATENT DOCUMENTS

| | | | |
|---|---|---|---|
| CA | 2 013 729 C | * 4/1990 | ............ A01N 33/20 |
| CN | 101330826 A | 12/2008 | |
| EP | 0077078 A1 | 4/1983 | |
| EP | 0453915 A1 | 10/1991 | |
| JP | 08-053306 A | 2/1996 | |
| JP | 08-099805 A | 4/1996 | |
| JP | 10-287510 A | 10/1998 | |
| JP | 2000-247821 A | 9/2000 | |
| JP | 2005-170956 A | 6/2005 | |
| JP | 2005-527608 A | 9/2005 | |
| JP | 2007-186497 A | 7/2007 | |
| WO | 8800184 A1 | 1/1988 | |
| WO | 95013698 A1 | 5/1995 | |
| WO | 03051116 A1 | 6/2003 | |
| WO | 2008149962 A1 | 12/2008 | |

OTHER PUBLICATIONS

Surfactants as Dispersants and Stabilisation of Suspensions: retrieved from internet: http://onlinelibrary.wiley.com/doi/10.1002/3527604812.ch7/summary. retrieved on Jul. 15, 2013.*
Office Action issued Mar. 8, 2013 in CN Application No. 201080039559.5.
Int'l Search Report issued Dec. 14, 2010 in Int'l Application No. PCT/JP2010/065457.
Extended European Search Report issued Sep. 5, 2013 in EP Application No. 10815400.6.

(Continued)

*Primary Examiner* — Ernst V Arnold
*Assistant Examiner* — Hong Yu
(74) *Attorney, Agent, or Firm* — Panitch Schwarze Belisario & Nadel LLP

(57) ABSTRACT

A microcapsule in which a liquid droplet is coated with a resin, wherein in the droplet, a pesticidally active solid ingredient is suspended in a compound of formula (I), wherein R represents a C1-C5 alkyl group, is useful as a formulation of a pesticidally active solid ingredient.

(I)

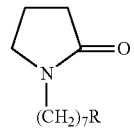

15 Claims, No Drawings

(56) References Cited

OTHER PUBLICATIONS

Office Action issued May 13, 2014 in JP Application No. 2009-209063.
English translation of an Office Action issued Oct. 21, 2013 in CN Application No. 201080039559.5.
English translation of an Office Action issued Jan. 27, 2014 in CN Application No. 201080039559.5.
English translation of an Office Action issued Dec. 4, 2013 in MX Application No. MX/a/2012/001740.
Office Action issued Jul. 7, 2014 in TW Application No. 099128091.

* cited by examiner

MICROCAPSULE AND PRODUCTION METHOD THEREOF

CROSS-REFERENCE TO RELATED APPLICATION

This application is a Section 371 of International Application No. PCT/JP2010/065457, filed Sep. 2, 2010, which was published in the English language on Mar. 17, 2011, under International Publication No. WO 2011/030805 A1, and the disclosure of which is incorporated herein by reference.

TECHNICAL FIELD

The present invention relates to a microcapsule and a production method thereof.

BACKGROUND ART

As a microcapsule containing a pesticidal compound of high water solubility, it is known that a microcapsule in which a liquid droplet is coated with a resin, wherein in tha droplet, a pesticidal compound is suspended in a certain kind of fatty ester (see, JP-A No. 2007-186497)

DISCLOSURE OF INVENTION

The present invention provides a novel microcapsule containing a pesticidally active ingredient of high water solubility and a production method thereof. Further, the present invention provides a microcapsule containing simultaneously a pesticidal compound of high water solubility and a pesticidal compound of low water solubility, and a production method thereof.

The present invention is as described below.

[1] A microcapsule in which a liquid droplet is coated with a resin, wherein in the droplet, a pesticidally active solid ingredient is suspended in a compound of formula (I):

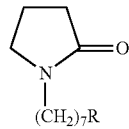

(I)

wherein R represents a C1-C5 alkyl group.

[2] The microcapsule according to [1], wherein the pesticidally active solid ingredient is composed of two or more solid pesticidal compounds.

[3] The microcapsule according to [2], wherein the two or more solid pesticidal compounds are composed of at least one solid pesticidal compound whose water solubility at 20° C. is more than 100 ppm and at least one solid pesticidal compound whose water solubility at 20° C. is less than 30 ppm.

[4] The microcapsule according to [1], wherein the pesticidally active solid ingredient is a neonicotinoid compound.

[5] The microcapsule according to [1], wherein the pesticidally active solid ingredient is clothianidin.

[6] The microcapsule according to [3], wherein the solid pesticidal compound of whose water solubility at 20° C. is more than 100 ppm is clothianidin.

[7] The microcapsule according to [3], wherein the solid pesticidal compound of whose water solubility at 20° C. is more than 100 ppm is furametpyr.

[8] The microcapsule according to any one of [1] to [7], wherein the resin is a polyurethane resin or a polyurea resin.

[9] A method of producing a microcapsule, wherein
(1) a pesticidally active solid ingredient is suspended in a compound of formula (I) defined in [1],
(2) the resultant suspension is mixed with water to give oil liquid droplets emulsified in water,
(3) a coating film of a resin is formed around the liquid droplet.

[10] A method of microcapsule production, wherein
(1) a pesticidally active solid ingredient is suspended in a mixture of a compound of formula (I) defined in [1] and a polyisocyanate,
(2) the resultant suspension is mixed with water to give oil liquid droplets emulsified in water,
(3) the polyisocyanate in the liquid droplet is reacted with a polyol or a polyamine to form a coating film of a resin around the liquid droplet.

[11] A method of microcapsule production, wherein
(1) at least one solid pesticidal compound whose water solubility at 20° C. is more than 100 ppm and at least one solid pesticidal compound whose water solubility at 20° C. is less than 30 ppm are suspended in a compound of formula (I) defined in [1],
(2) the resultant suspension is mixed with water to give oil liquid droplets emulsified in water,
(3) a coating film of a resin is formed around the liquid droplet.

[12] A method of microcapsule production, wherein
(1) at least one solid pesticidal compound whose water solubility at 20° C. is more than 100 ppm and at least one solid pesticidal compound whose water solubility at 20° C. is less than 30 ppm are suspended in a compound of formula (I) defined in [1],
(2) the resultant suspension is mixed with water to give oil liquid droplets emulsified in water,
(3) an anionic surfactant is added to the emulsion containing the liquid droplet, and then, a coating film of a resin is formed around the liquid droplet.

[13] A method of microcapsule production, wherein
(1) at least one solid pesticidal compound whose water solubility at 20° C. is more than 100 ppm and at least one solid pesticidal compound whose water solubility at 20° C. is less than 30 ppm are suspended in a mixture of a compound of formula (I) defined in [1] and a polyisocyanate,
(2) the resultant suspension is mixed with water to give oil liquid droplets emulsified in water,
(3) an anionic surfactant is added to the emulsion containing the liquid droplet, and then, the polyisocyanate in the liquid droplet is reacted with a polyol or a polyamine to form a coating film of a resin around the liquid droplet.

[14] The method of microcapsule production according to [12] or [13], wherein the anionic surfactant is a salt of lignin-sulfonic acid.

[15] A microcapsule produced by the method according to any one of [9] to [14].

The microcapsule of the present invention is capable of containing an pesticidal compound of high water solubility. The microcapsule of the present invention is capable of simultaneously containing an pesticidal compound of high water solubility and an pesticidal compound of low water solubility.

MODE FOR CARRYING OUT THE INVENTION

The pesticidally active solid ingredient in the present invention is composed of at least one solid pesticidal compound.

Such a solid pesticidal compound is usually an pesticidally active compound whose melting point is 30° C. or more, preferably 50° C. or more, and a compound having a solubility in a compound of formula (I) of 5 wt % or less is preferable.

The solid pesticidal compound includes insecticidal compounds, fungicidal compounds, herbicidal compounds, insect growth-regulating compounds, plant growth-regulating compounds and insect repellent compounds. Specific examples thereof include the following compounds.

Examples of the insecticidal compound include carbamate compounds such as propoxur, isoprocarb, xylylcarb, metolcarb, XMC, carbaryl, pyrimicarb, carbofuran, methomyl, phenoxycarb, alanycarb, metoxadiazone and so on; organophosphorus compounds such as acephate, phenthoate, vamidothion, trichlorfon, monocrotophos, tetrachlorvinphos, dimethylvinphos, phosalone, chlorpyrifos, chlorpyrifos-methyl, pyridafenthion, quinalphos, methidathion, methamidophos, dimethoate, azinphos-ethyl, azinphos-methyl, salithion and so on; neonicotinoid compounds such as imidacloprid, nitenpyram, acetamiprid, clothianidin, thiamethoxam and so on; cartap, buprofezin, thiocyclam, bensultap, phenoxycarb, fenazaquin, fenpyroximate, pyridaben, hydramethylnon, thiodicarb, chlorfenapyr, fenproximate, pymetrozine, pyrimidifen, tebufenozide, tebufenpyrad, triazamate, indoxacarb MP, sulfluramid, milbemectin, avermectin, and p-dichlorobenzene.

Examples of the fungicidal compound include benzimidazole compounds such as benomyl, carbendazim, thiabendazol, thiophanate-methyl and so on; phenyl carbamate compounds such as diethofencarb and so on; dicarboxylmide compounds such as procymidone, iprodione, vinclozolin and so on; azole compounds such as diniconazole, epoxyconazole, tebuconazole, difenoconazole, cyproconazole, flusilazole, triadimefon, simeconazole and so on; acylalanine compounds such as metalaxyl and so on; carboxamide compounds such as furametpyr, mepronil, flutolanil, thifluzamide, metalaxyl and so on; organophosphorus compounds such as triclofos-methyl, fosetyl, pyrazophos and so on; anilinopyrimidine compounds such as pyrimethanil, mepanipyrim, cyprodinil and so on; phenylpyrrole compounds such as fludioxonil and so on; chlorothalonil, acibenzolar-S-methyl, isoprothiolane, diclomezine, pencycuron, fluoroimide, dithianon, chinomethionat, diflumetorim, triazine, iminoctadine acetate, iminoctadine albesil acetate, propamocarb hydrochloride, cyazofamid, fexamid, cyflufenamid, tiadinil, kasugamycin, manzeb, captan, folpet, tricyclazole, pyroquilon, probenazole, fthalide, cymoxanil, dimethomorph, famoxadone, oxolinic acid and its salts, fluazinam, ferimzone and diclocymet.

Examples of the herbicidal compound include triazine compounds such as simazine, atrazine, simetryn, prometryn, dimethametryn, cyanidin, triaziflam, metribuzin, metamitron and so on; urea compounds such as isoproturon and so on; nitrile compounds such as ioxynil and so on; dinitroaniline compounds such as trifluralin, prodiamine, pendimethalin, oryzalin and so on; aromatic carboxylic acid compounds such as dicamba, imazaquin, dithiopyr, fentrazamide and so on; sulfonylurea compounds such as bensulfuron-methyl, ethoxysulfuron, pyrazosulfuron-ethyl, azimsulfuron, halosulfuron-methyl, flazasulfuron, cinosulfuron, nicosulfuron, rymsulfuron, thifensulfuron-methyl, imazosulfuron, metosulfuron-methyl, cyclosulfamuron, sodium salt of trifloxysulfuron and so on; sulfentrazone, paraquat, flumeturam, triflusulfron-methyl, fenoxaprop-p-ethyl, cyhalofop-butyl, diflufenican, norflurazone, isoxaflutole, ammonium salt of glufosinate, glyphosate salts, bentazone, mefenacet, propanil, flumiclorac-pentyl, and flumioxazine.

Examples of the insect growth-regulating compound include diflubenzuron, teflubenzuron, lufenuron, flufenoxuron, chlorofluazuron, novaluron, tebufenozide, chromafenozide, methoxyfenozide, buprofezin, cyromazine and pyriproxyfen.

Examples of the plant growth-regulating compounds include ethephon, indolebutyric acid, ethychlozate, 1-naphthylacetamide, 4-CPA, benzylaminopurine, forchlorfenuron, gibberellin, uniconazole P, chlormequat, paclobutrazole, flurprimidol, trinexapac-ethyl, and daminozide.

Microcapsulation according to the present invention is possible even if the pesticidally active solid ingredient is a high water-soluble pesticidal compound whose water solubility at 20° C. is 100 mg/L or more, providing that it is suspended in a compound of formula (I) and dispersed in the form of a solid particle.

In the present invention, in the case of a pesticidally active solid ingredient to be suspended in a compound of formula (I) and dispersed in the form of a solid particle, even if the pesticidally active solid ingredient is composed of two or more solidpesticidal compounds, these two or more pesticidal compounds can be contained simultaneously in a microcapsule. In this case, it may also be permissible that at least one solid pesticidal compound is a high water-soluble pesticidal compound whose water solubility at 20° C. is more than 100 ppm and at least one solid pesticidal compound is a low water-soluble pesticidal compound whose water solubility at 20° C. is less than 30 ppm. That is, the microcapsule of the present invention can also contain simultaneously a high water-soluble solid pesticidal compound and a low water-soluble solid pesticidal compound as the pesticidally active solid ingredient.

Examples of the low water-soluble pesticidal compound to be used in the present invention include pesticidal compounds whose water solubility at 20° C. is less than 10 ppm.

Examples of the high water-soluble pesticidal compound whose water solubility at 20° C. is more than 100 ppm include clothianidin, tricyclazole, furametpyr and ferimzone.

Examples of the low water-soluble pesticidal compound whose water solubility at 20° C. is less than 30 ppm include procymidone, flumioxazin and fthalide.

Examples of the compound of formula (I) include compounds of formula (I) in which R represents a methyl group and compounds of formula (I) in which R represents a pentyl group.

In the microcapsule of the present invention, the liquid droplet in the microcapsule is a suspension of a pesticidally active solid ingredient in a compound of formula (I). In the microcapsule of the present invention, as the organic solvent constituting the liquid droplet in the microcapsule, a compound of formula (I) may be singly used. The organic solvent constituting the liquid droplet in the microcapsule may also be a mixture of a compound of formula (I) and other organic solvent.

The amount of the pesticidally active solid ingredient in the liquid droplet to the amount of a compound of formula (I) by weight is usually 5/100 to 100/100, preferably 5/100 to 40/100, further preferably 10/100 to 30/100.

In the present invention, the particle diameter of the pesticidally active solid ingredient particle suspended in the liquid droplet is usually 10 μm or less, preferably in the range of 100 nm to 5 μm, in terms of volume median diameter. It is preferable that the cumulative volume of particles having a particle diameter of 20 μm or more is 10% or less.

The volume median diameter can be measured, for example, by Mastersizer 2000 (trade name of Malvern Instruments).

In the present invention, the particle diameter of the liquid droplet in the microcapsule is approximately the same as the particle size of the microcapsule. The particle size of the microcapsule is in the range of usually 1 to 80 μm, preferably 1 to 50 μm, in terms of volume median diameter.

In the present invention, examples of the resin to form a coating film of the microcapsule include polyurethane resins, polyurea resins, polyamide resins, polyester resins, aminoplast resins, urea formalin resins and melamine formalin resins. In the present invention, as the resin to form a coating film of the microcapsule, polyurethane resins or polyurea resins are preferable from the standpoint of storage stability of the microcapsule.

In the present invention, the amount of the resin to form a coating film of the microcapsule is usually in the range of 0.01 to 30 wt % with respect to the whole amount of the microcapsule.

Coating of the liquid droplet with a resin is usually carried out by forming a coating film of a resin by an interfacial polymerization method. The method of forming a coating film of a resin by an interfacial polymerization method is a method in which an oil-soluble raw material among two raw materials forming a resin is previously dissolved in a suspension of a pesticidally active solid ingredient, while a water-soluble raw material among two raw materials forming a resin is previously dissolved in water for dispersing the suspension, and a polymerization reaction of these two raw materials is caused at an interface between the suspended liquid droplet and water. The thickness of a coating film can be calculated from the particle diameter of the liquid droplet and the amount of the resin constituting the coating film.

The polyurethane resin to be used as a coating film of the microcapsule of the present invention is usually obtained by reacting a polyisocyanate and a polyol.

The polyurea resin to be used as a coating film of the microcapsule of the present invention is usually obtained by reacting a polyisocyanate and a polyamine.

Examples of the polyisocyanate include hexamethylene diisocyanate, an adduct of hexamethylene diisocyanate and trimethylolpropane, a Biuret condensate of three molecules of hexamethylene diisocyanate, an adduct of tolylene diisocyanate and trimethylolpropane, an isocyanurate condensate of tolylene diisocyanate, an isocyanurate condensate of hexamethylene diisocyanate, an isocyanurate condensate of isophorone diisocyanate; an isocyanate prepolymer in which one isocyanate part of hexamethylene diisocyanate constitutes an isocyanurate body together with two molecules of tolylene diisocyanate and another isocyanate part thereof constitutes an isocyanurate body together with other two molecules of hexamethylene diisocyanate; 4,4'-methylenebis (cyclohexyl isocyanate), and trimethyl hexamethylene diisocyanate. In the present invention, use is preferably made of an adduct of tolylene diisocyanate and trimethylolpropane, an isocyanurate condensate of tolylene diisocyanate, an isocyanurate condensate of hexamethylene diisocyanate or an isocyanurate condensate of isophorone diisocyanate.

Examples of the polyol include ethylene glycol, propylene glycol, butylene glycol and cyclopropanediol. Examples of the polyamine include ethylenediamine, hexamethylenediamine, diethylenetriamine and triethylenetetramine.

The microcapsule of the present invention is used as an pesticidal composition in the form of an aqueous suspension composition dispersed in water. In the pesticidal composition, the microcapsule is dispersed in water, further, if necessary, additives such as a thickening agent, anti-freezing agent, preservative, agent for controlling specific gravity are added. The weight of water in the pesticidal composition is usually 0.3 to 3 times with respect to the weight of the microcapsule.

Next, the method of producing a microcapsule of the present invention will be described.

This method comprises (1) a first step in which a pesticidally active solid ingredient is suspended in a compound of formula (I), (2) a second step in which the resultant suspension is mixed with water to give oil liquid droplets emulsified in water, and (3) a third step in which a coating film of a resin is formed around the liquid droplet.

The step in which a pesticidally active solid ingredient is suspended in a compound of formula (I) can be carried out, for example, by the following methods (a) and (b).

(a) A method of dry-pulverizing a pesticidally active solid ingredient and mixing the pulverized pesticidally active solid ingredient with a compound of formula (I).

Examples of the method of dry-pulverizing a pesticidally active solid ingredient include air mill pulverization and mechanical pulverization. In dry-pulverizing a pesticidally active solid ingredient, a pulverizer can be used. Examples of the pulverizer include JOM-0101-type jet pulverizer (manufactured by Seishin Enterprise Co., Ltd.) and counter jet mill (manufactured by Hosokawa Micron Corporation). In the present invention, a pesticidally active solid ingredient is pulverized usually into a volume median diameter of 10 μm or less, preferably into a volume median diameter in the range of 100 nm to 5 μm, by dry pulverization. In the pulverized pesticidally active solid ingredient, it is preferable that the cumulative volume of particles having a particle diameter of 20 μm or more is 10% or less.

By mixing the pesticidally active solid ingredient pulverized by dry pulverization with a compound of formula (I) and further stirring the mixture, a suspension can be obtained in which the pesticidally active solid ingredient is suspended in the compound of formula (I). When the pesticidally active solid ingredient is composed of two or more solid pesticidal compounds, it is also possible to pulverize the two or more solid pesticidal compounds by dry pulverization, thereby allowing the two or more pulverized solid pesticidal compounds to be suspended in a compound of formula (I).

(b) A method of wet-pulverizing a pesticidally active solid ingredient in a compound of formula (I).

The step in which a pesticidally active solid ingredient is suspended in a compound of formula (I) can be carried out by wet-pulverizing a pesticidally active solid ingredient in a compound of formula (I).

Examples of the method of wet-pulverizing a pesticidally active solid ingredient in a compound of formula (I) include methods in which to a compound of formula (I) is added a pesticidally active solid ingredient, and if necessary, beads for pulverization and so on, and the mixture is wet-pulverized using a pulverizer. Examples of the pulverizer to be used include mills such as a bead mill, ball mill, rod mill and so on. Specific examples of the pulverizer include Dyno Mill (manufactured by Willy A. Bachofen Ag. Maschinenfabrik), colloid mill (manufactured by Primix Corporation) and Gamma Grain Mill (manufactured by Asada Iron Works Co., Ltd.). As a rotor-stator type homogenizer, for example, POLYTRON homogenizer (manufactured by Kinematica AG) is specifically mentioned.

In the present invention, a pesticidally active solid ingredient is pulverized usually into a volume median diameter of 10 μm or less, preferably into a volume median diameter in the range of 100 nm to 5 μm, by wet pulverization. In the pulverized pesticidally active solid ingredient, it is preferable that the cumulative volume of particles having a particle diameter of 20 μm or more is 10% or less. When the pesticidally active solid ingredient is composed of two or more solid pesticidal compounds, it is also possible that to a compound of formula (I) is added the two or more solid pesticidal compounds, and if necessary, beads for pulverization and so on, and the mixture is wet-pulverized using a pulverizer.

The operation of pulverizing a pesticidally active solid ingredient in a compound of formula (I) can also be produced by two or more operations. For example, in pulverizing a pesticidally active solid ingredient in a compound of formula (I), it is also possible to coarsely pulverize a pesticidally active solid ingredient in a first operation, and to further finely pulverize a pesticidally active solid ingredient in a second operation. As the method of carrying out the operation of pulverizing a pesticidally active solid ingredient in a compound of formula (I) in two operations, for example, a method is mentioned in which a rotor-stator type homogenizer is used as the pulverizer in the first operation, and a mill is used in the second operation.

The pesticidally active solid ingredient to be suspended in a compound of formula (I) in the first step may be composed of a single solid pesticidal compound, or may be composed of two or more solid pesticidal compounds. In the case of two or more solid pesticidal compounds, a combination of at least one high water-soluble solid pesticidal compound and at least one low water-soluble solid pesticidal compound may also be permissible.

When the resin to form a coating film is a polyurethane resin or a polyurea resin, the suspension to be used in the second step can be obtained by the following methods.
(1) A method which a pesticidally active solid ingredient is suspended in a mixture of a compound of formula (I) and a polyisocyanate.
(2) A method which a polyisocyanate is added into a suspension prepared by suspending a pesticidally active solid ingredient in a compound of formula (I).

It is preferable that the suspension obtained in the first step is used quickly in the subsequent step.

For preparing oil liquid droplets emulsified in water by mixing the suspension and water in the second step, it is usual that the suspension obtained in the first step is added to water, and stirred using a stirring machine. Examples of the stirring machine used in this case include stirring machines such as a propeller stirring machine, turbine stirring machine, high-speed shear stirring machine and so on, and specific examples of the stirring machine include T. K. Homo Mixer (manufactured by PRIMIX Corporation), Clearmix (manufactured by M Technique Co., Ltd.), POLYTRON homogenizer and MEGATRON homogenizer (KINEMATICA).

Regarding the weight ratio of the suspension to water, the amount of water is usually in the range of 0.8 to 2 times with respect to the weight of the suspension. It is preferable to use deionized water as the water to be mixed with the suspension. In the water to be mixed with the suspension, if necessary, additives such as a thickening agent, anti-freezing agent, preservative, agent for controlling specific gravity may be added.

Examples of the thickening agent include natural polysaccharides such as xanthan gum, rhamsan gum, locust bean gum, carrageenan, welan gum and so on, synthetic polymers such as polyvinyl alcohol, polyvinylpyrrolidone, sodium polyacrylate and so on, semi-synthetic polymers such as carboxymethylcellulose and so on, mineral powders such as aluminum magnesium silicate, smectite, bentonite, hectorite, dry silica and so on, and alumina sol. Examples of the anti-freezing agent include propylene glycol. Examples of the preservative include p-hydroxybenzoate esters, salicylic acid derivatives and isothiazoline derivatives. Examples of the agent for controlling specific gravity include water-soluble salts such as sodium sulfate and so on, and water-soluble compounds such as urea and so on.

The suspension has low viscosity, thus, when the suspension and water are mixed by a stirring machine, it is dispersed relatively easily in water to form oil liquid droplets. Since strong stirring is not required in dispersing, there is little restriction on an equipment for carrying out this step. Also in the case of use of a pesticidally active solid ingredient having high water solubility, the pesticidally active ingredient is maintained as a solid particle in a compound of formula (I), thus, the pesticidally active solid ingredient scarcely moves into an aqueous phase, and liquid droplets can be prepared.

When the resin to form a coating film is a polyurethane resin, a polyol is previously added into water for dispersing the suspension, or a polyol is added into an aqueous phase after the second step. When the resin to form a coating film is a polyurea resin, a polyamine is previously added into water for dispersing the suspension, or a polyamine is added after the second step.

It is preferable that the water dispersion of the liquid droplet obtained in the second step is quickly used in the subsequent step.

When at least one high water-soluble solid pesticidal compound and at least one low water-soluble solid pesticidal compound are simultaneously contained in a microcapsule, it is preferable to add an anionic surfactant to the water dispersion of the liquid droplet obtained in the second step before performing the third step. By addition of an anionic surfactant, the liquid droplet in the water dispersion is stabilized.

Examples of the anionic surfactant include sodium salt of ligninsulfonic acid, sodium naphthalenesulfonate-formalin condensate, sodium alkylnaphthalenesulfonate-formalin condensate, sodium polyacrylate, sodium polyacrylate-sodium maleate copolymer, and sodium polystyrenesulfonate. The amount of the anionic surfactant to be used in producing a microcapsule of the present invention is usually in the range of 0.1 to 10 wt % with respect to the water dispersion of the oil liquid droplets obtained in the second step.

In the third step, the method for forming a coating film of a resin around the liquid droplet is not particularly restricted, and usual microcapsulation methods can be used such as an interfacial polymerization method, In-situ polymerization method and so on. The interfacial polymerization method is carried out, for example, by heating a water dispersion of oil liquid droplets containing previously added raw materials to a temperature at which a polymerization reaction progresses, adding one of raw materials forming a resin to an aqueous phase of a water dispersion of oil liquid droplets, or activating one of raw materials forming a resin by pH regulation.

When the resin to form a coating film is a polyurethane resin, for example, a water dispersion of oil liquid droplets is heated at 40 to 80° C. while stirring and maintained for about 0.5 to 48 hours, thereby forming a coating film of a polyurethane resin around the liquid droplet.

When the resin to form a coating film is a polyurea resin, for example, a water dispersion of oil liquid droplets is maintained at 0 to 50° C. for about 0.5 to 48 hours, thereby forming a coating film of a polyurea resin around the liquid droplet.

In thus obtained microcapsule aqueous suspension composition, most of pesticidally active solid ingredients are present as a solid particle in the microcapsule, and the amount of pesticidally active ingredients dissolved or suspended in water outside the coating film of the microcapsule is much small compared with the total pesticidally active ingredient amount.

The microcapsule aqueous suspension composition of the present invention obtained by the above-described method can also be used as a microcapsule powdery preparation by centrifugal separation, filtration, spray dry and so on. Further, to this microcapsule aqueous suspension composition, a thickening agent, anti-freezing agent, preservative, agent for controlling specific gravity, water and so on can be further added.

The microcapsule of the present invention is used, for example, as an pesticidal composition containing a pesticidally active solid ingredient in an amount of 0.1 to 30 wt % based on the total aqueous suspension composition amount.

When the pesticidally active solid ingredient is an insecticidal compound, an pesticidal composition containing a microcapsule of the present invention is applied by spraying, for example, to an insect pest or an insect pest, in a proportion of about 0.1 to 1000 g/1000 m$^2$, preferably about 1 to 100 g/1000 m$^2$ in terms of the amount of the pesticidally active solid ingredient.

When the pesticidally active solid ingredient is a fungicidal compound, an pesticidal composition containing a microcapsule of the present invention is applied by spraying, for example, to a plant which a plant disease causes or a plant which a plant disease will cause, in a proportion of about 0.1 to 1000 g/1000 m$^2$, preferably about 1 to 100 g/1000 m$^2$ in terms of the amount of the pesticidally active solid ingredient.

When the pesticidally active solid ingredient is a herbicidal compound, an pesticidal composition containing a microcapsule of the present invention is applied by spraying, for example, to a weed or a habitat where a weed will grow, in a proportion of about 0.1 to 1000 g/1000 m$^2$, preferably about 1 to 100 g/1000 m$^2$ in terms of the amount of the pesticidally active solid ingredient.

EXAMPLES

The present invention will be explained by examples below, but the present invention is not limited to these examples.

First, examples are shown for production of a microcapsule of the present invention.

Example 1

Clothianidin was dry-pulverized by JOM-0101-type jet pulverization apparatus (manufactured by Seishin Enterprise Co., Ltd.). The volume median diameter of the pulverized clothianidin (hereinafter, referred to as pulverized clothianidin) was measured by a laser mode particle size distribution measuring instrument Mastersizer 2000 (manufactured by Malvern Instruments Ltd.) to find a value of 2.8 μm.

To 10 g of the pulverized clothianidin was added 30 g of a compound of formula (I) in which R represents a methyl group and 0.2 g of a polyisocyanate (Desmodur L75; manufactured by Sumika Bayer Urethane Co., Ltd.) and the mixture was stirred at room temperature for 20 minutes, to obtain a suspension.

To 1840 g of deionized water was added 160 g of polyvinyl alcohol (Arabiccol SS); manufactured by San-Ei Yakuhin-Boeki Co., Ltd.) and the mixture was stirred at room temperature for 60 minutes, to obtain a polyvinyl alcohol 8% aqueous solution (hereinafter, referred to as present polyvinyl alcohol aqueous solution). To 60 g of the present polyvinyl alcohol aqueous solution was added the above-described suspension, and the mixture was stirred by T.K. Auto Homo Mixer (manufactured by PRIMIX Corporation; 3000 rpm) for 5 minutes, to give oil liquid droplets emulsified in water. To the resultant mixture was added 0.06 g of diethylenetriamine. This mixture was thermally insulated at 50° C. for 3 hours, thereby forming a coating film of a polyurea around oil liquid droplets, to obtain a microcapsule aqueous suspension.

To 88.64 g of deionized water was added 0.6 g of aluminum magnesium silicate (Veegum granules; manufactured by Vanderbilt Co., Ltd.), and this mixture was stirred at room temperature for 60 minutes. To the resultant mixture was added 0.3 g of xanthan gum (Kelzan S; manufactured by CP Kelco) and 10 g of propylene glycol, and the mixture was stirred at 60° C. for 60 minutes. This mixture was cooled down to room temperature, and 0.2 g of a preservative (Proxel GXL; manufactured by Arch Chemicals Inc.) was added to this mixture, to give a thickening agent aqueous solution. This thickening agent aqueous solution was added to the above-described microcapsule aqueous suspension, to obtain an aqueous suspension formulation containing clothianidin in a proportion of 50.

Example 2

An aqueous suspension formulation containing clothianidin in a proportion of 5% was obtained in the same manner as in Example 1 excepting that 30 g of the compound of formula (I) in which R represents a methyl group was changed to 30 g of a compound of formula (I) in which R represents a pentyl group.

Example 3

Ferimzone was dry-pulverized by JOM-0101-type jet pulverization apparatus. The volume median diameter of the pulverized ferimzone (hereinafter, referred to as pulverized ferimzone) was measured by a laser mode particle size distribution measuring instrument Mastersizer 2000 to find a value of 3.1 μm.

An aqueous suspension formulation containing ferimzone in a proportion of 5% was obtained in the same manner as in Example 1 excepting that 10 g of the pulverized clothianidin was changed to 10 g of pulverized ferimzone.

Example 4

An aqueous suspension formulation containing ferimzone in a proportion of 5% was obtained in the same manner as in Example 3 excepting that 30 g of the compound of formula (I) in which R represents a methyl group was changed to 30 g of a compound of formula (I) in which R represents a pentyl group.

Example 5

Tricyclazole was dry-pulverized by JOM-0101-type jet pulverization apparatus. The volume median diameter of the pulverized tricyclazole (hereinafter, referred to as pulverized tricyclazole) was measured by a laser mode particle size distribution measuring instrument Mastersizer 2000 to find a value of 2.4 μm.

An aqueous suspension formulation containing tricyclazole in a proportion of 5% was obtained in the same manner as in Example 1 excepting that 10 g of the pulverized clothianidin was changed to 10 g of pulverized tricyclazole.

Example 6

An aqueous suspension formulation containing tricyclazole in a proportion of 5% was obtained in the same manner as in Example 2 excepting that 10 g of the pulverized clothianidin was changed to 10 g of pulverized tricyclazole.

Example 7

To 7.5 g of pulverized ferimzone, 7.5 g of pulverized tricyclazole and 3.3 g of pulverized clothianidin were added 43 g of a compound of formula (I) in which R represents a methyl group and 0.2 g of a polyisocyanate (Desmodur L75), and the mixture was stirred at room temperature for 20 minutes, to obtain a suspension.

To 92 g of the present polyvinyl alcohol aqueous solution was added the above-described suspension, and the mixture was stirred by T.K. Auto Homo Mixer (3000 rpm) for 5 minutes, to give oil liquid droplets emulsified in water. To the resultant mixture was added 0.06 g of diethylenetriamine and 4 g of sodium salt of ligninsulfonic acid (New Calgen WG4; manufactured by Takemoto Oil & Fat Co., Ltd.). This mixture was thermally insulated at 50° C. for 3 hours, thereby forming a coating film of a polyurea around oil liquid droplets, to obtain a microcapsule suspension.

To 31.34 g of deionized water was added 0.6 g of aluminum magnesium silicate (Veegum granules), and this mixture was stirred at room temperature for 60 minutes. To the resultant mixture was added 0.3 g of xanthan gum (Kelzan S) and 10 g of propylene glycol, and the mixture was stirred at 60° C. for 60 minutes. This mixture was cooled down to room temperature, and 0.2 g of a preservative (Proxel GXL) was added to this mixture, to give a thickening agent aqueous solution. This thickening agent aqueous solution was added to the above-described microcapsule suspension, to obtain an aqueous suspension formulation containing ferimzone in a proportion of 3.75%, tricyclazole in a proportion of 3.75% and clothianidin in a proportion of 1.65%.

Example 8

An aqueous suspension formulation containing ferimzone in a proportion of 3.75%, tricyclazole in a proportion of 3.75% and clothianidin in a proportion of 1.65% was obtained in the same manner as in Example 7 excepting that 43 g of the compound of formula (I) in which R represents a methyl group was changed to 43 g of a compound of formula (I) in which R represents a pentyl group.

Example 9

Furametpyr was dry-pulverized by JOM-0101-type jet pulverization apparatus. The volume median diameter of the pulverized furametpyr (hereinafter, referred to as pulverized furametpyr) was measured by a laser mode particle size distribution measuring instrument Mastersizer 2000 to find a value of 2.8 μm.

Flumioxazin was dry-pulverized by JOM-0101-type jet pulverization apparatus. The volume median diameter of the pulverized flumioxazin (hereinafter, referred to as pulverized flumioxazin) was measured by a laser mode particle size distribution measuring instrument Mastersizer 2000 to find a value of 3.5 μm.

To 6 g of the pulverized furametpyr and 6 g of the pulverized flumioxazin were added 42 g of a compound of formula (I) in which R represents a methyl group and 0.04 g of a polyisocyanate (Desmodur L75), and the mixture was stirred at room temperature for 20 minutes to obtain a suspension.

To 70.2 g of the present polyvinyl alcohol aqueous solution was added the above-described suspension, and the mixture was stirred by T.K. Auto Homo Mixer (3000 rpm) for 5 minutes, to give oil liquid droplets emulsified in water. To the resultant mixture was added 0.03 g of diethylenetriamine and 2 g of sodium salt of ligninsulfonic acid (New Calgen WG4). This mixture was thermally insulated at 50° C. for 3 hours, thereby forming a coating film of a polyurea around oil liquid droplets, to obtain a microcapsule suspension.

To 62.63 g of deionized water was added 0.6 g of aluminum magnesium silicate (Veegum granules), and this mixture was stirred at room temperature for 60 minutes. To the resultant mixture was added 0.3 g of xanthan gum (Kelzan S) and 10 g of propylene glycol, and the mixture was stirred at 60° C. for 60 minutes. This mixture was cooled down to room temperature, and 0.2 g of a preservative (Proxel GXL) was added to this mixture, to give a thickening agent aqueous solution. This thickening agent aqueous solution was added to the above-described microcapsule suspension, to obtain an aqueous suspension formulation containing furametpyr in a proportion of 3% and flumioxazin in a proportion of 3%.

Example 10

Fthalide was dry-pulverized by JOM-0101-type jet pulverization apparatus. The volume median diameter of the pulverized fthalide (hereinafter, referred to as pulverized fthalide) was measured by a laser mode particle size distribution measuring instrument Mastersizer 2000 to find a value of 3.8 μm.

An aqueous suspension formulation containing ferimzone in a proportion of 3.75%, fthalide in a proportion of 3.75% and clothianidin in a proportion of 1.65% was obtained in the same manner as in Example 7 excepting that 7.5 g of the pulverized ferimzone, 7.5 g of the pulverized tricyclazole and 3.3 g of the pulverized clothianidin were changed to 7.5 g of pulverized ferimzone, 7.5 g of pulverized fthalide and 3.3 g of pulverized clothianidin.

Example 11

To 6 g of pulverized procymidone and 6 g of pulverized furametpyr were added 42 g of a compound of formula (I) in which R represents a methyl group and 0.2 g of a polyisocyanate (Desmodur L75), and the mixture was stirred at room temperature for 20 minutes to obtain a suspension.

To 70.2 g of the present polyvinyl alcohol aqueous solution was added the above-described suspension, and the mixture was stirred by T.K. Auto Homo Mixer (3000 rpm) for 5 minutes, to give oil liquid droplets emulsified in water. To the resultant mixture was added 0.2 g of ethylene glycol and 4 g of sodium salt of ligninsulfonic acid (New Calgen WG4). This mixture was thermally insulated at 65° C. for 24 hours, thereby forming a coating film of a polyurethane around oil liquid droplets, to obtain a microcapsule aqueous suspension.

To 60.3 g of deionized water was added 0.6 g of aluminum magnesium silicate (Veegum granules), and this mixture was stirred at room temperature for 60 minutes. To the resultant mixture was added 0.3 g of xanthan gum (Kelzan S; manufactured by CP Kelco) and 10 g of propylene glycol, and this mixture was stirred at 60° C. for 60 minutes. This mixture was cooled down to room temperature, and 0.2 g of a preservative (Proxel GXL) was added to this mixture, to give a thickening agent aqueous solution. This thickening agent aqueous solution was added to the above-described microcapsule aqueous suspension, to obtain an aqueous suspension formulation containing procymidone in a proportion of 3% and furametpyr in a proportion of 3%.

Example 12

To 4 g of pulverized procymidone, 4 g of pulverized furametpyr and 4 g of pulverized fthalide were added 42 g of a compound of formula (I) in which R represents a pentyl group and 0.2 g of a polyisocyanate (Desmodur L75), and the mixture was stirred at room temperature for 20 minutes to obtain a suspension.

To 80 g of the present polyvinyl alcohol aqueous solution was added the above-described suspension, and the mixture was stirred by T.K. Auto Homo Mixer (3000 rpm) for 5 minutes, to give oil liquid droplets emulsified in water. To the resultant mixture was added 0.2 g of ethylene glycol and 4 g of sodium salt of ligninsulfonic acid (New Calgen WG4). This mixture was thermally insulated at 65° C. for 24 hours, thereby forming a coating film of a polyurethane around oil liquid droplets, to obtain a microcapsule aqueous suspension.

To 50.5 g of deionized water was added 0.6 g of aluminum magnesium silicate (Veegum granules), and this mixture was stirred at room temperature for 60 minutes. To the resultant mixture was added 0.3 g of xanthan gum (Kelzan S) and 10 g of propylene glycol, and this mixture was stirred at 60° C. for 60 minutes. This mixture was cooled down to room temperature, and 0.2 g of a preservative (Proxel GXL) was added to this mixture, to give a thickening agent aqueous solution. This thickening agent aqueous solution was added to the above-described microcapsule aqueous suspension, to obtain an aqueous suspension formulation containing procymidone in a proportion of 2%, furametpyr in a proportion of 2% and fthalide in a proportion of 2%.

Comparative Example 1

To 10 g of pulverized clothianidin was added 48 g of methyl O-acetyl ricinoleate (RIC-CIZER C-101; manufactured by Itoh Oil Chemicals Co., Ltd.) and 13.2 g of a polyisocyanate (Desmodur L75; manufactured by Sumika Bayer Urethane Co., Ltd.), and the mixture was stirred at room temperature to obtain a suspension.

To 83.82 g of deionized water was added 6.7 g of gum Arabic (Arabiccol SS; manufactured by San-Ei Yakuhin Boeki Co., Ltd.), and the mixture was stirred at room temperature to obtain an aqueous phase. To this aqueous phase was added the above-described suspension, and the mixture was stirred by T.K. Auto Homo Mixer (manufactured by PRIMIX Corporation; 4000 rpm) for 5 minutes, to give oil liquid droplets emulsified in water. To the resultant mixture was added 1.22 g of diethylenetriamine. This mixture was thermally insulated at 50° C. for 3 hours, thereby forming a coating film of polyurea around oil liquid droplets, to obtain a microcapsule aqueous suspension.

To 27.66 g of deionized water was added 0.6 g of aluminum magnesium silicate (Veegum granules; manufactured by Vanderbilt Co., Inc.), and this mixture was stirred at room temperature for 60 minutes. To the resultant mixture was added 0.3 g of xanthan gum (Kelzan S; manufactured by CP Kelco) and 10 g of propylene glycol, and the mixture was stirred at 60° C. for 60 minutes. This mixture was cooled down to room temperature, and to this mixture was added 0.2 g of a preservative (Proxel GXL; manufactured by Arch Chemicals Inc) to give a thickening agent aqueous solution. This thickening agent aqueous solution was added to the above-described microcapsule aqueous suspension, to obtain an aqueous suspension formulation containing clothianidin in a proportion of 7.5%.

Test Example

The aqueous suspension formulation containing clothianidin obtained in Example 1 and the aqueous suspension formulation containing clothianidin obtained in Comparative Example 1 were diluted with water containing a spreading agent (Dine; manufactured by Sumitomo Chemical Garden Products Inc.) in an amount of 1/5000 (v/v) so as to give a clothianidin concentration of 50 ppm and a clothianidin concentration of 100 ppm, respectively. In this diluted solution, cabbage leaves were immersed for 60 seconds. The cabbage leaves were air-dried sufficiently. The cabbage leaves were placed in a polyethylene cup having a volume of 240 ml. In this polyethylene cup, 20 *Plutella xylostella* first instar larvae were placed. The number of survived insects was checked 2 days after and 5 days after, and the controlling value was calculated by the following formula (repeated twice).

controlling value=100×($A-B/A$)     Formula:

A: survival rate of *Plutella xylostella* in non-treated area with medical agent B: survival rate of *Plutella xylostella* in treated area with medical agent The results are shown in Table 1.

TABLE 1

| Used medical agent | Concentration (ppm) | 2 days after | 5 days after |
|---|---|---|---|
| | | Controlling value | |
| Example 1 | 50 | 100 | 100 |
| | 100 | 100 | 100 |
| Comparative Example 1 | 50 | 13.8 | 40 |
| | 100 | 24.1 | 80 |

INDUSTRIAL APPLICABILITY

The microcapsule of the present invention is useful as a formulation of a pesticidally active solid ingredient.

The invention claimed is:

1. A microcapsule in which a liquid droplet is coated with a resin, wherein in the droplet, a pesticidally active solid ingredient is suspended as solid particles in a compound of formula (I):

(I)

[structure: pyrrolidinone with N-(CH$_2$)$_7$R substituent]

wherein R represents a $C_1$-$C_5$ alkyl group.

2. The microcapsule according to claim 1, wherein the pesticidally active solid ingredient is composed of two or more solid pesticidal compounds.

3. The microcapsule according to claim 2, wherein the two or more solid pesticidal compounds are composed of at least one solid pesticidal compound whose water solubility at 20° C. is more than 100 ppm and at least one solid pesticidal compound whose water solubility at 20° C. is less than 30 ppm.

4. The microcapsule according to claim 1, wherein the pesticidally active solid ingredient is a neonicotinoid compound.

5. The microcapsule according to claim 1, wherein the pesticidally active solid ingredient is clothiamdin.

6. The microcapsule according to claim 3, wherein the solid pesticidal compound whose water solubility at 20° C. is more than 100 ppm is clothianidin.

7. The microcapsule according to claim 3, wherein the solid pesticidal compound whose water solubility at 20° C. is more than 100 ppm is furametpyr.

8. The microcapsule according to claim 1, wherein the resin is a polyurethane resin or a polyurea resin.

9. A method of producing a microcapsule, wherein:
(1) a pesticidally active solid ingredient is suspended as solid particles in a compound of formula (I):

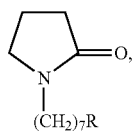

wherein R represents a $C_1$-$C_5$ alkyl group;
(2) the resultant suspension is mixed with water to give oil liquid droplets emulsified in water; and
(3) a coating film of a resin is formed around the liquid droplet.

10. The method of microcapsule production according to claim 9, wherein:
(1) a pesticidally active solid ingredient is suspended as solid particles in a mixture of a compound of formula (I):

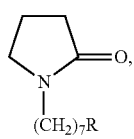

wherein R represents a $C_1$-$C_5$ alkyl group, and a polyisocyanate;
(2) the resultant suspension is mixed with water to give oil liquid droplets emulsified in water; and
(3) the polyisocyanate in the liquid droplet is reacted with a polyol or a polyamine to form a coating film of a resin around the liquid droplet.

11. The method of microcapsule production according to claim 9, wherein:
(1) at least one solid pesticidal compound whose water solubility at 20° C. is more than 100 ppm and at least one solid pesticidal compound whose water solubility at 20° C. is less than 30 ppm are suspended as solid particles in a compound of formula (I):

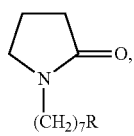

wherein R represents a $C_1$-$C_5$ alkyl group;
(2) the resultant suspension is mixed with water to give oil liquid droplets emulsified in water; and
(3) a coating film of a resin is formed around the liquid droplet.

12. The method of microcapsule production according to claim 9, wherein:
(1) at least one solid pesticidal compound whose water solubility at 20° C. is more than 100 ppm and at least one solid pesticidal compound whose water solubility at 20° C. is less than 30 ppm are suspended as solid particles in a compound of formula (I):

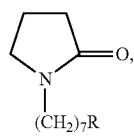

wherein R represents a $C_1$-$C_5$ alkyl group;
(2) the resultant suspension is mixed with water to give oil liquid droplets emulsified in water; and
(3) an anionic surfactant is added to the emulsion containing the liquid droplet, and then, a coating film of a resin is formed around the liquid droplet.

13. The method of microcapsule production according to claim 9, wherein:
(1) at least one solid pesticidal compound whose water solubility at 20° C. is more than 100 ppm and at least one solid pesticidal compound whose water solubility at 20° C. is less than 30 ppm are suspended as solid particles in a mixture of a compound of formula (I):

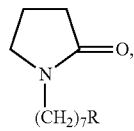

wherein R represents a $C_1$-$C_5$ alkyl group and a polyisocyanate;
(2) the resultant suspension is mixed with water to give oil liquid droplets emulsified in water; and
(3) an anionic surfactant is added to the emulsion containing the liquid droplet, and then, the polyisocyanate in the liquid droplet is reacted with a polyol or a polyamine to form a coating film of a resin around the liquid droplet.

14. The method of microcapsule production according to claim 12, wherein the anionic surfactant is a salt of ligninsulfonic acid.

15. A microcapsule produced by the method according to claim 9.

* * * * *